United States Patent [19]

Broekaert et al.

[11] Patent Number: 5,750,504
[45] Date of Patent: May 12, 1998

[54] ANTIMICROBIAL PROTEINS

[75] Inventors: Willem Frans Broekaert, Dilbeek; Bruno Philippe Angelo Cammue, Alsemberg, both of Belgium; Rupert William Osborn, Twickenham; Sarah Bronwen Rees, Forest Park, both of United Kingdom

[73] Assignee: Zeneca Agrochemicals, England

[21] Appl. No.: 656,318

[22] PCT Filed: Dec. 19, 1994

[86] PCT No.: PCT/GB94/02766

§ 371 Date: Jun. 12, 1996

§ 102(e) Date: Jun. 12, 1996

[87] PCT Pub. No.: WO95/18229

PCT Pub. Date: Jul. 6, 1995

[51] Int. Cl.$^6$ ............................ A61K 38/00; C12N 13/00
[52] U.S. Cl. .................................... 514/12; 530/324
[58] Field of Search .......................... 800/205; 530/300, 530/324; 435/69.1; 514/44, 12

[56] References Cited

FOREIGN PATENT DOCUMENTS

| 93 05153 | 3/1993 | WIPO . |
|---|---|---|
| 94 16076 | 7/1994 | WIPO . |

OTHER PUBLICATIONS

Stitt et al., Regulation of metabolism in transgenic plants. Annu. Rev. Plant Physiol. Plant Mol. Biol., vol. 46, pp. 341–368, 1995.

*Primary Examiner*—John Lebuyader
*Assistant Examiner*—Andrew Wang
*Attorney, Agent, or Firm*—Cushman Darby & Cushman IP Group of Pillsbury Madison & Sutro LLP

[57] ABSTRACT

Antimicrobial proteins capable of isolation from seeds of Heuchera or Aesculus show a wide range of antifungal activity and some activity against Gram-positive bacteria. DNA encoding the proteins may be isolated and incorporated into vectors. Plants transformed with this DNA may be produced. The proteins find commercial application as antifungal or antibacterial agents; transformed plants will show increased disease-resistance.

5 Claims, 5 Drawing Sheets

| SPECIES (protien) | SEQUENCE |
|---|---|
| Raphanus Sativus (Rs-AFP1) | ZKLC-ERPSGTWSGVCGNNNACKNQCINLEK-ARHGSCNYVFPAHKCICYFPC |
| Raphanus Sativus (Rs-AFP2) | ZKLC-QRPSGTWSGVCGNNNACKNQCIRLEK-ARHGSCNYVFPAHKCICYFPC |
| Heuchera Sanguinea (Hs-AFP1) | DGVKLC-DVPSGTWSGHCGSSSKCSQQCKDREHFAYGACHYQFPSVKCFCKRQC |
| Aesculus Hippocastanum (Ah-AMP1) | LCNERPSQTWSGNCGNTAHCDKQCQDWEK-ASHGACHKRENHWKCFCYFNC |
| Dahlia Merckii (Dm-AMP1) | ELC-EKASKTWSGNCGNTGHCDNQCKSWEG-AAHGACHVRNGKHMCFCYFNC |
| Cnicus Benedictus (Cb-AMP1) | ELC-EKASKTWSGNCGNTKHCDDQCKSWEG-AAHGACHVRNGKHMCFCYFNC |
| Clitoria Ternatea (Ct-AMP1) | NLC-ERASLTWTGNCGNTGHCDTQCRNWES-AKHGACHKR-GNWKCFCYFDC |
| Lathyrus Cicera (Lc-AFP) | KTC-ENLSGTFKGPCIPDGNCNKHCKNNEH-LLSGRCRDDF---?CWCTRNC |
| Vigna Unguiculata (pSAS10) | KTC-ENLVDTYRGPCFTTGSCDDHCKNKEH-LLSGRCRDDV---RCWCTRNC |
| Pisum Sativum (p1230) | NTC-ENLAGSYKGVCFGG--CDRHCRTQEG-AISGRCRDDF---RCWCTKNC |
| Sorghum Bicolor (Siα2) | RVC-MGKSAGFKGLCMRDQNCAQVCL-QEG-WGGGNCDGVM-RQCKCIRQCW |
| Triticum Aestivum (γ1-P) | KIC-RRRSAGFKGPCMSNKNCAQVCQ-QEG-WGGGNCDGPF--RRCKCIRQC |
| Solanum Tubersum (P322) | RHC-ESLSHRFKGPCTRDSNCASVCET-ER-FSGGNCHGFR--RRCFCTKPC |
| Consensus Motif | --C------Y-G-C------C----E----G-C------C--C---C-<br>F<br>W |

FIG. 5

ANTIMICROBIAL PROTEINS

This application is a 371 of International application PCT/GB94/02766, filed Dec. 19, 1994.

This invention relates to antimicrobial proteins, processes for their manufacture and use, and DNA sequences encoding them. In particular it relates to antimicrobial proteins capable of being isolated from seeds of Heuchera or Aesculus.

In this context, antimicrobial proteins are defined as proteins possessing at least one of the following activities: antifungal activity (which may include anti-yeast activity) or antibacterial activity. Activity includes a range of antagonistic effects such as partial inhibition or death. Such proteins may be oligomeric or may be single peptide subunits.

The genus Heuchera is part of the Saxifragaceae plant family. The Saxifragaceae is a large widespread family comprising mainly perennial herbs and shrubs, containing the currants and gooseberries as well as many popular garden flowers.

The genus Aesculus is part of the Hippocastanaceae plant family. The Hippocastanaceae is a small family of trees comprising two genera. The genus Aesculus is best known for its ornamental trees, notably the horse chestnut (*Aesculus hippocastanum*) whose brown seeds are the "conkers" much prized by children.

Plants produce a wide array of antifungal compounds to combat potential invaders and over the last ten years it has become clear that proteins with antifungal activity form an important part of these defenses. Several classes of such proteins have been described including thionins, beta-1,3-glucanases, ribosome-inactivating proteins, zeamatins, chitin-binding lectins and chitinases. These proteins have gained considerable attention as they could potentially be used as biocontrol agents.

International Patent Application Number PCT/GB92/01570 (published on 18 Mar., 1993 under the publication number WO93/05153, the disclosure of which is incorporated herein by reference) describes a protein class comprising antifungal proteins (AFPs) and antimicrobial proteins (AMPs). The class includes the following proteins: Rs-AFP1 and Rs-AFP2 capable of isolation from *Raphanus sativus* (Terras FRG et al, 1992, J Biol Chem, 267:15301-13309), Bn-AFP1 and Bn-AFP2 capable of isolation from *Brassica napus*, Br-AFP1 and Br-AFP2 capable of isolation from *Brassica rapa*, Sa-AFP1 and Sa-AFP2 capable of isolation from *Sinapis alba*, At-AFP1 capable of isolation from *Arabidopsis thaliana*, Dm-AMP1 and Dm-AMP2 capable of isolation from *Dahlia merckii*, Cb-AMP1 and Cb-AMP2 capable of isolation from *Cnicus benedictus*, Lc-AFP capable of isolation from *Lathyrus cicera*, Ct-AMP1 and Ct-AMP2 capable of isolation from *Clitoria ternatea*. This protein class will hereinafter be referred to as "the Rs-AFP-type proteins". These and other plant-derived antimicrobial proteins are useful as fungicides or antibiotics, particularly for agricultural purposes. The proteins may be applied to or around a plant or may be expressed within a plant.

We have now purified two new potent antimicrobial proteins.

We have purified a new antimicrobial protein from seeds of *Heuchera sanquinea*, hereinafter called Hs-AFP1 (*Heuchera sanquinea*—antifungal protein 1). Hs-AFP1 is a 5 kDa polypeptide; such polypeptides may be associated as dimers. Hs-AFP1 shows a wide range of antifungal activity.

We have also purified a new antimicrobial protein from seeds of *Aesculus hippocastanum*, hereinafter called Ah-AMP1 (*Aesculus hippocastanum*—antimicrobial protein 1). Like Hs-AFP1, Ah-AMP1 is a 5 kDa polypeptide. Ah-AMP1 shows a wide range of antifungal activity.

According to the present invention, there is provided an antimicrobial protein having an amino acid sequence as shown in SEQ ID NO 1 or SEQ ID NO 2, or an amino acid sequence which is substantially homologous to SEQ ID NO 1 or SEQ ID NO 2 (preferably having at least 60% sequence identity) provided that such a protein has antimicrobial activity.

An antimicrobial protein according to the invention is capable of being isolated from seeds of Heuchera or Aesculus, and may also be capable of isolation from the seeds of both related and unrelated species, or may be produced or synthesised by any suitable method.

The antimicrobial protein may be extracted and purified from plant material, manufactured from its known amino acid sequence by chemical synthesis using a standard peptide synthesiser, or produced within a suitable organism (for example, a micro-organism or plant) by expression of recombinant DNA. The antimicrobial protein is useful as a fungicide or an antibiotic and may be used for agricultural or pharmaceutical applications.

Amino acid sequencing of Hs-AFP1 and of Ah-AMP1 shows that they are homologous to the Rs-AFP-type proteins (International Patent Application Publication Number WO93/05153). The amino acid sequence of Hs-AFP1 is shown as SEQ ID NO 1; the amino acid sequence of Ah-AMP1 is shown as SEQ ID NO 2.

Figure 5:
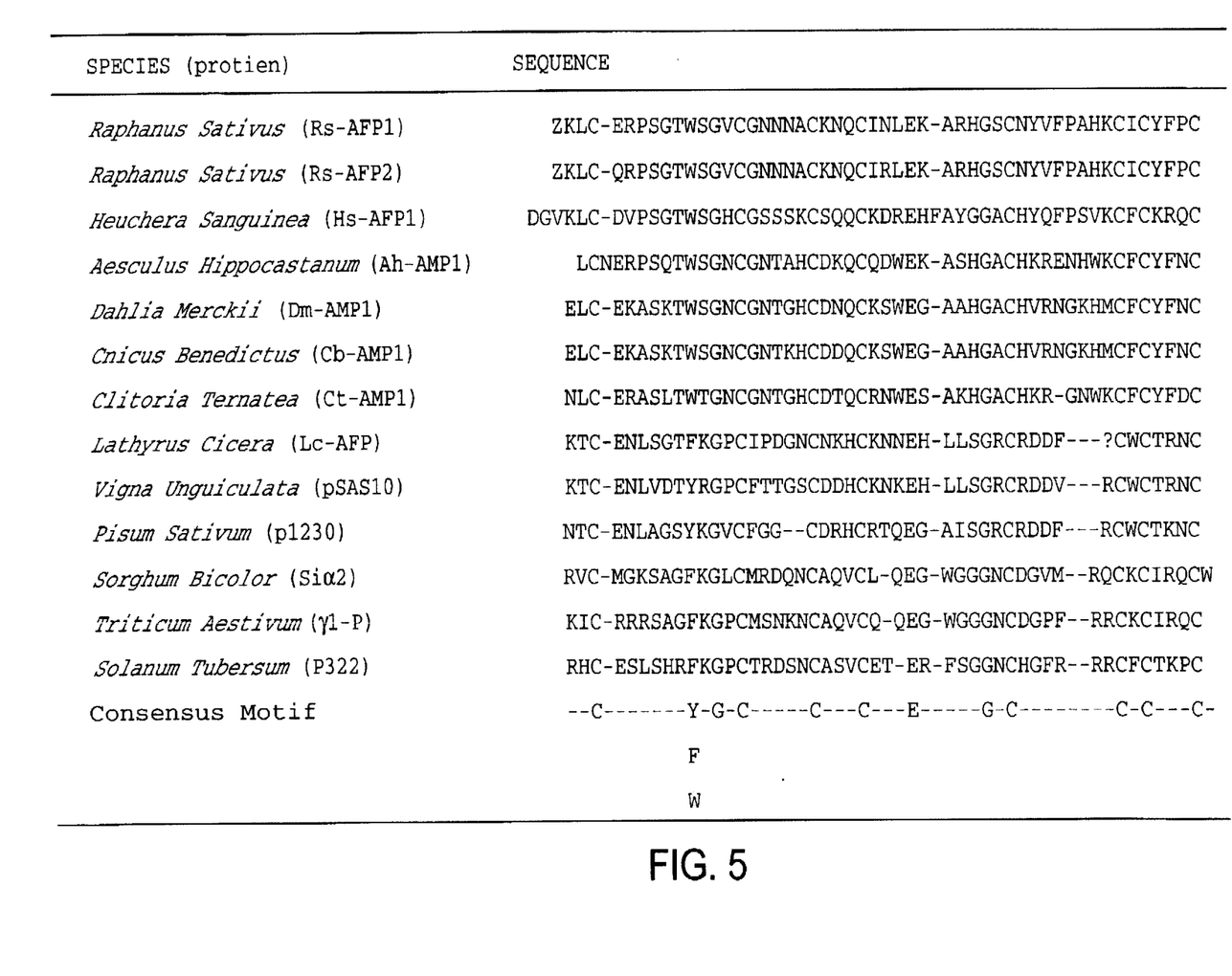

FIG. 5 shows the sequence alignment of Hs-AFP1 (SEQ ID NO 1) and Ah-AMP1 (SEQ ID NO 2) with the Rs-AFP-type antifungal/antimicrobial proteins Rs-AFP1 (SEQ ID NO 3), Rs-AFP2 (SEQ ID NO 4), Dm-AMP1 (SEQ ID NO 5), Cb-AMP1 (SEQ ID NO 6), Ct-AMP1 (SEQ ID NO 7) and Lc-AFP (SEQ ID NO 8) as described in International Patent Application Publication Number WO93/05153. Part of the sequences of the proteins Siα2 from Sorghum (SEQ ID NO 9) and g1-P from Triticum (SEQ ID NO 10), plus the predicted gene products of pSAS10 (Vigna) (SEQ ID NO 11), pI230 (Pisum) (SEQ ID NO 12) and p322 (Solanum) (SEQ ID NO 13) are also shown (discussed hereinafter). Dashes have been introduced into the sequences to give optimal alignment.

The Rs-AFP-type proteins share a common structural motif which is also found within the sequences of Hs-AFP1 and of Ah-AMP1. Sequence alignment of Hs-AFP1 and Ah-AMP1 with the Rs-AFP-type proteins shows that they share a consensus cysteine-glycine motif which is shown in FIG. 5. It is clear from FIG. 5 that the number of amino acid residues between the conserved cysteines and glycines varies slightly in the different sequences and partial sequences shown: dashes have been introduced into the sequences to give optimal alignment. With residue numbering relative to the sequence of Hs-AFP1, all eight cysteine residues have conserved positions at residue numbers 6, 17, 23, 27, 39, 48, 50 and 54 and there are two conserved glycines at position numbers 15 and 37. In addition, there is a conserved aromatic residue at position 13, and a conserved glutamate residue at position 31.

The Hs-AFP1 sequence shows 48% sequence identity with Rs-AFP1. The Ah-AMP1 sequence shows 54% sequence identity with Rs-AFP1. Hs-AFP1 shows 52% identity to Ah-AMP1 on the amino acid sequence level. Despite the similarities between the Heuchera protein (Hs-AFP1), the Aesculus protein (Ah-AMP1) and the Rs-AFP-type proteins, there are differences in overall amino acid content and sequence.

The antifungal activity of Hs-AFP1 causes severe branching (hyper-branching) of fungal hyphae from certain species. This morphological effect is similar to that produced by Rs-AFP1 or Rs-AFP2. The protein Ah-AMP1, while inhibiting fungal growth, does not cause hyper-branching of hyphae. This activity is more similar to that of the proteins Dm-AMP1, Cb-AMP1, Ct-AMP1 and Lc-AFP.

Hs-AFP1, AH-AMP1 and the Rs-AFP-type proteins are partially homologous to the predicted protein products of the Fusarium-induced genes pI39 and pI230 in pea (*Pisum sativum*—a member of the Fabaceae family) as described by Chiang and Hadwiger (1991, Mol Plant Microbe Interact, 4:324–331). This homology is shared with the predicted protein product of the PSAS10 gene from cowpea (*Vigna unquiculata*—another Fabaceae) as described by Ishibashi et al (1990, Plant Mol Biol, 15:59–64). The proteins are also partially homologous with the predicted protein product of gene p322 in potato (*Solanum tuberosum*—a member of the Solanaceae family) as described by Stiekema et al (1988, Plant Mol Biol, 11:255–269). Recently a protein whose amino-terminal amino acid sequence is almost identical to the mature protein encoded by p322 has been purified from potato tubers and shown to possess antimicrobial activity (Moreno et al, 1994, Eur J Biochem, 233:135–139). Nothing is known about the biological properties of the proteins encoded by genes pI39, pI230, pSAS10 or p322 as only the cDNA has-been studied. However, the pI39 and pI230 genes are switched on after challenge to the plant by a disease or other stress. It has been proposed that the pSAS10 gene encodes a protein involved in germination.

The Hs-AFP1, Ah-AMP1 and Rs-AFP-type protein sequences show a lower degree of partial homology with the sequences of a group of small α-amylase inhibitors found in the following members of the Gramineae: sorghum (Bloch and Richardson, 1991, FEBS Lett, 279:101–104), wheat (Colitta et al, 1990, FEBS Lett, 270:191–194) and barley (Mendez et al, 1990 Eur J Biochem, 194:533–539). Such proteins, including Siα2 from sorghum and g-1-purothionin (g-1P) from wheat, are known to inhibit insect α-amylase and may be toxic to insect larvae although this has never been shown. It is not known if these α-amylase inhibitors show any antifungal or other antimicrobial activity; no other data on their biological activity has been reported.

Knowledge of its primary structure enables manufacture of the antimicrobial protein, or parts thereof, by chemical synthesis using a standard peptide synthesiser. It also enables production of DNA constructs encoding the antimicrobial protein.

The invention further provides a DNA sequence encoding an antimicrobial protein according to the invention. The DNA sequence may be a cDNA sequence or a genomic sequence, and may be derived from a cDNA clone, a genomic DNA clone or DNA manufactured using a standard nucleic acid synthesiser.

The DNA sequence may be predicted from the known amino acid sequence and DNA encoding the protein may be manufactured using a standard nucleic acid synthesiser. Alternatively, the DNA sequence may be isolated from plant-derived DNA libraries. Suitable oligonucleotide probes may be derived from the known amino acid sequence and used to screen a cDNA library for CDNA clones encoding some or all of the protein. These same oligonucleotide probes or cDNA clones may be used to isolate the actual antimicrobial protein gene(s) by screening genomic DNA libraries. Such genomic clones may include control sequences operating in the plant genome. Thus it is also possible to isolate promoter sequences which may be used to drive expression of the antimicrobial (or other) proteins. These promoters may be particularly responsive to environmental conditions (such as the presence of a fungal pathogen), and may be used to drive expression of any target gene.

The DNA sequence encoding the antimicrobial protein may be-incorporated into a DNA construct or vector in combination with suitable regulatory sequences (promoter, terminator, etc). The DNA sequence may be placed under the control of a constitutive or an inducible promoter (stimulated by, for example, environmental conditions, presence of a pathogen, presence of a chemical). Such a DNA construct may be cloned or transformed into a biological system which allows expression of the encoded protein or an active part of the protein. Suitable biological systems include micro-organisms (for example, bacteria such as *Escherichia coli*, Pseudomonas and endophytes such as *Clavibacter xyli* subsp. *cynodontis* (Cxc); yeast; viruses; bacteriophages; etc), cultured cells (such as insect cells, mammalian cells) and plants. In some cases, the expressed protein may subsequently be extracted and isolated for use.

An antimicrobial protein according to the invention (such as Hs-AFP1 or Ah-AMP1) is useful as a fungicide or an antibiotic. The invention further provides a process of combating fungi or bacteria whereby they are exposed to an antimicrobial protein according to the invention.

For pharmaceutical applications, the antimicrobial protein may be used as a fungicide or anti-bacterial to treat mammalian infections (for example, to combat yeasts such as Candida).

An antimicrobial protein according to the invention may also be used as a preservative (for example, as a food additive).

For agricultural applications, the antimicrobial protein may be used to improve the disease-resistance or disease-tolerance of crops either during the life of the plant or for post-harvest crop protection. Pathogens exposed to the proteins are inhibited. The antimicrobial protein may eradicate a pathogen already established on the plant or may protect the plant from future pathogen attack. The eradicant effect of the protein is particularly advantageous.

Exposure of a plant pathogen to an antimicrobial protein may be achieved in various ways, for example:

(a) a composition comprising the isolated protein may be applied to plant parts or the surrounding soil using standard agricultural techniques (such as spraying); the protein may have been extracted from plant tissue or chemically synthesised or extracted from micro-organisms genetically modified to express the protein;

(b) a composition comprising a micro-organism genetically modified to express the antimicrobial protein may be applied to a plant or the soil in which a plant grows;

(c) an endophyte genetically modified to express the antimicrobial protein may be introduced into the plant tissue (for example, via a seed treatment process);

[An endophyte is defined as a micro-organism having the ability to enter into non-pathogenic endosymbiotic relationships with a plant host. A method of endophyte-enhanced protection of plants has been described in a series of patent applications by Crop Genetics International Corporation (for example, International Application Publication Number WO90/13224, European Patent Publication Number EP-125468-B1, International Application Publication Number WO91/10363, International Application Publication Number WO87/03303). The endophyte may be genetically modified to produce agricultural chemicals. International Patent Application Publication Number WO94/16076

(ZENECA Limited) describes the use of endophytes which have been genetically modified to express a plant-derived antimicrobial protein].

(d) DNA encoding an antimicrobial protein may be introduced into the plant genome so that the protein is expressed within the plant body (the DNA may be cDNA, genomic DNA or DNA manufactured using a standard nucleic acid synthesiser).

Plant cells may be transformed with recombinant DNA constructs according to a variety of known methods (Agrobacterium Ti plasmids, electroporation, microinjection, microprojectile gun, etc). The transformed cells may then in suitable cases be regenerated into whole plants in which the new nuclear material is stably incorporated into the genome. Both transformed monocotyledonous and dicotyledonous plants may be obtained in this way, although the latter are usually more easy to regenerate. Some of the progeny of these primary transformants will inherit the recombinant DNA encoding the antimicrobial protein(s).

The invention further provides a plant having improved resistance to a fungal or bacterial pathogen and containing recombinant DNA which expresses an antimicrobial protein according to the invention. Such a plant may be used as a parent in standard plant breeding crosses to develop hybrids and lines having improved fungal or bacterial resistance.

Recombinant DNA is heterologous DNA which has been introduced into the plant or its ancestors by transformation. The recombinant DNA encodes an antimicrobial protein expressed for delivery to a site of pathogen attack (such as the leaves). The DNA may encode an active subunit of an antimicrobial protein.

A pathogen may be any fungus or bacterium growing on, in or near the plant. In this context, improved resistance is defined as enhanced tolerance to a fungal or bacterial pathogen when compared to a wild-type plant. Resistance may vary from a slight increase in tolerance to the effects of the pathogen (where the pathogen in partially inhibited) to total resistance so that the plant is unaffected by the presence of pathogen (where the pathogen is severely inhibited or killed). An increased level of resistance against a particular pathogen or resistance against a wider spectrum of pathogens may both constitute an improvement in resistance. Transgenic plants (or plants derived therefrom) showing improved resistance are selected following plant transformation or subsequent crossing.

Where the antimicrobial protein is expressed within a transgenic plant or its progeny, the fungus or bacterium is exposed to the protein at the site of pathogen attack on the plant. In particular, by use of appropriate gene regulatory sequences, the protein may be produced in vivo when and where it will be most effective. For example, the protein may be produced within parts of the plant where it is not normally expressed in quantity but where disease resistance is important (such as in the leaves).

Examples of genetically modified plants which may be produced include field crops, cereals, fruit and vegetables such as: canola, sunflower, tobacco, sugarbeet, cotton, soya, maize, wheat, barley, rice, sorghum, tomatoes, mangoes, peaches, apples, pears, strawberries, bananas, melons, potatoes, carrot, lettuce, cabbage, onion.

BRIEF DESCRIPTION OF THE DRAWINGS

The invention will now be described by way of example only with reference to the drawings, in which:

FIG. 5 shows the amino acid sequence alignment of Hs-AFP1, Ah-AMP1 and other proteins; and with reference to the SEQUENCE LISTING in which:

SEQ ID NO 1 is the amino acid sequence of Hs-AFP1;
SEQ ID NO 2 is the amino acid sequence of AH-AMP1;
SEQ ID NO 3 is the amino acid sequence of Rs-AFP1;
SEQ ID NO 4 is the amino acid sequence of Rs-AFP2;
SEQ ID NO 5 is the amino acid sequence of Dm-AMP1;
SEQ ID NO 6 is the amino acid sequence of Cb-AMP1;
SEQ ID NO 7 is the amino acid sequence of Ct-AMP1;
SEQ ID NO 8 is the amino acid sequence of Lc-AFP;
SEQ ID NO 9 is part of the amino acid sequence of Siα2;
SEQ ID NO 10 is part of the amino acid sequence of g1-P;
SEQ ID NO 11 is part of the predicted amino acid sequence of the pSAS10 gene product;
SEQ ID NO 12 is part of the predicted amino acid sequence of the pI230 gene product;
SEQ ID NO 13 is part of the predicted amino acid sequence of the p322 gene product.

EXAMPLE 1

Antifungal and antibacterial activity assays.

Antifungal activity was measured by microspectrophotometry as previously described (Broekaert, 1990, FEMS Microbiol Lett, 69:55–60). Routinely, tests were performed with 20 µl of a (filter-sterilized) test solution and 80 µl of a suspension of fungal spores ($2\times10^4$ spores/ml) in half strength potato dextrose broth (½ PDB). The synthetic growth medium (SMF) consisted of $K_2HPO_4$ (2.5 mM), $MgSO_4$ (50 µM), $CaCl_2$ (50 µM), $FeSO_4$ (5 µM), $CoCl_2$ (0.1 µM), $CuSO_4$ (0.1 µM), $Na_2MoO_4$ (2 µM), $H_3BO_3$ (0.5 µM), KI (0.1 µM), $ZNSO_4$ (0.5 µM), $MnSO_4$ (0.1 µM), glucose (10 g/l), asparagine (1 g/l), methionine (20 mg/l), myo-inositol (2 mg/l), biotin (0.2 mg/l), thiamine-HCl (1 mg/l), and pyridoxine-HCl (0.2 mg/l). Control microcultures contained 20 µl of sterile distilled water and 80 µl of the fungal spore suspension.

Unless otherwise stated the test organism was *Fusarium culmorum* (strain IMI 180420) and incubation was done at 25° C. for 48 hours. Percent growth inhibition is defined as 100 times the ratio of the corrected absorbance of the control microculture minus the corrected absorbance of the test microculture over the corrected absorbance at 595 nm of the control microculture. The corrected absorbance values equal the absorbance at 595 nm of the culture measured after 48 hours minus the absorbance at 595 nm measured after 30 min.

Antibacterial activity was measured microspectrophotometrically as follows. A bacterial suspension was prepared by inoculating soft nutrient agarose (tryptone, 10 g/l; Sea-plaque agarose (FMC), 5 g/l). Aliquots (80 µl) of the bacterial suspension ($10^5$ colony forming units per ml) were added to filter-sterilized samples (20 µl) in flat-bottom 96-well microplates. The absorbance at 595 nm of the culture was measured with the aid of a microplate reader after 30 minutes and 24 hours of incubation at 28° C. Percent growth inhibition was calculated as described above for the antifungal activity assay.

EXAMPLE 2
Purification of antifungal proteins from *Heuchera sanquinea* seeds.

Twenty grams of *H sanquinea* seeds (obtained from Okkerse, Mechelen, Belgium) was ground in a coffee mill and the resulting meal was extracted for 2 hours at 4° C. with 100 ml of an ice-cold extraction buffer containing 10 mM $NaH_2PO_4$, 15 mM $Na_2HPO_4$, 100 mM KCl, 2 mM EDTA, 2 mM thiourea, and 1 mM PMSF. The homogenate was squeezed through cheesecloth and clarified by centrifugation (30 min at 7,000× g). The supernatant was dialyzed extensively against distilled water using benzoylated cellulose tubing (Sigma) with a molecular weight cut off of 2,000 Da. After dialysis the solution was adjusted to 50 mM $(NH_4)Ac$ (pH 9) by addition of the ten-fold concentrated buffer, and subsequently passed over a Q-Sepharose Fast Flow (Pharmacia, Uppsala, Sweden) column (12×5 cm) in equilibrium with 50 mM $NH_4Ac$ (pH 9). The protein fraction passed through the column was lyophilyzed and finally redisolved in 50 ml 20 mM $NH_4Ac$ (ammonium acetate), pH6.

Figure 1A:
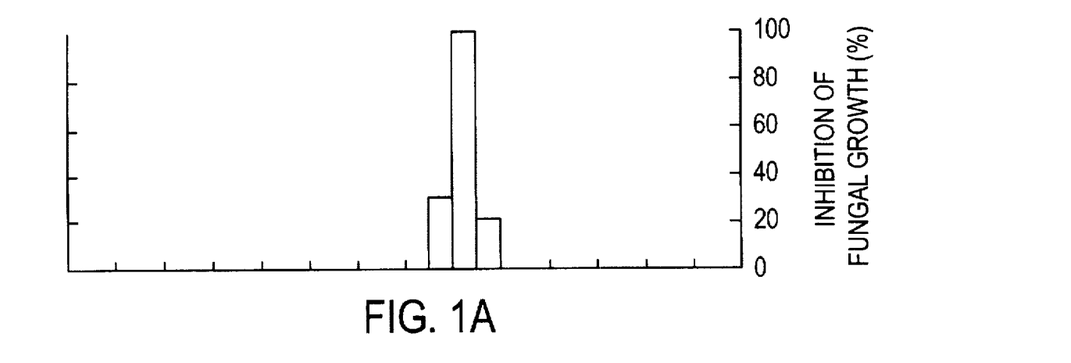
FIG. 1 shows the cation exchange chromatogram for purification of Hs-AFP1 and the associated graph of fungal growth inhibition.
Figure 1B:
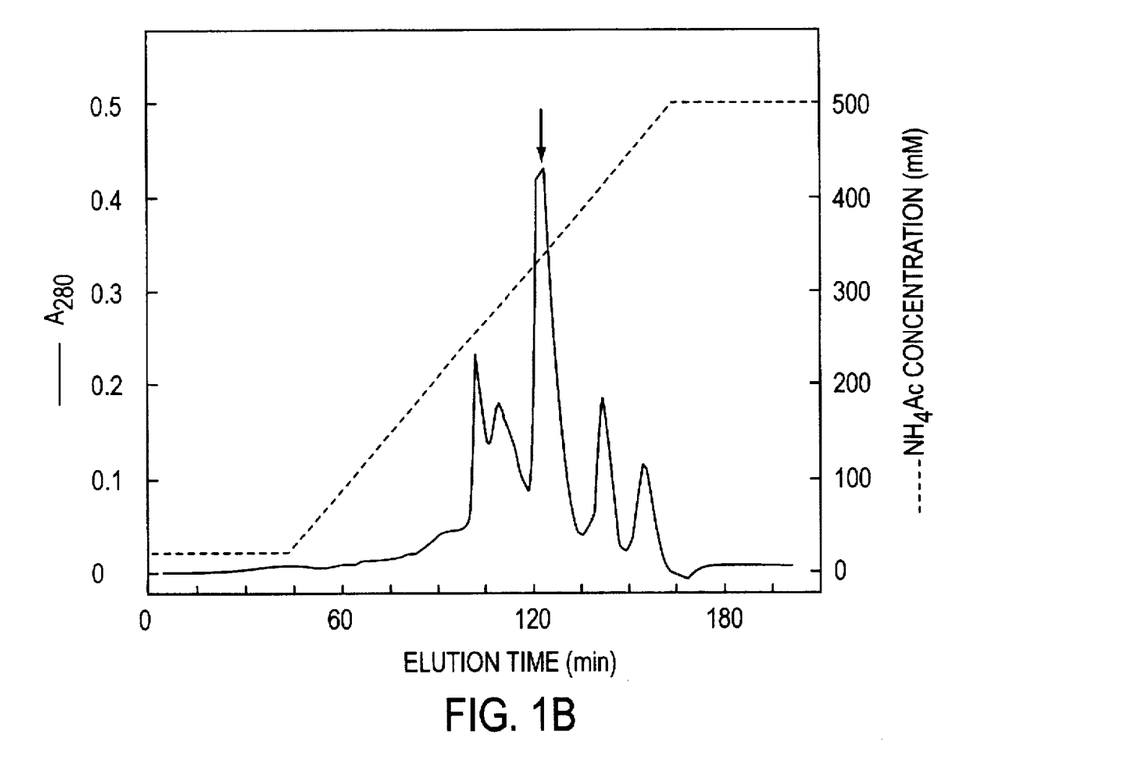

This fraction was applied on a S-Sepharose High Performance (Pharmacia) column (10×1.6 cm) previously equilibrated with 20 mM $NH_4Ac$ buffer. The column was eluted at 1 ml\min with a linear gradient of 120 ml from 20 to 500 mM $NH_4Ac$ (pH 6). The eluate was monitored for protein by online measurement of the absorbance at 280 nm (results shown in the lower panel of FIG. 1) and collected in 7.5 ml fractions.

The fractions were lyophilyzed and redissolved in distilled water. Of these fractions 5 μl was tested in the microspectrophotometric antifungal activity assays described in Example 1 using the synthetic growth medium supplemented with 1 mM $CaCl_2$ and 50 mM KCl (results shown as histograms in the upper panel of FIG. 1). All antifungal activity was contained in the major peak, which eluted at around 300 mM $NH_4Ac$ (indicated by an arrowhead in FIG. 1).

The fraction showing highest antifungal activity was further purified by reversed-phase chromatography. This fraction was loaded on a Pep-S (porous silica $C_2/C_{18}$, Pharmacia) column (25×0.93 cm) in equilibrium with 10% acetonitrile containing 0.1% TFA. The column was eluted at 4 ml/min with a linear gradient of 200 ml from 10% acetonitrile/0.1% trifluoroacetic acid (TFA) to 95% acetonitrile/0.1% TFA. The eluate was monitored for protein by online measurement of the absorption at 280 nm. Two ml fractions of the eluate were collected, vacuum-dried, and finally dissolved in 0.5 ml distilled water of which 10 μl was used in a microspectrophotometric antifungal activity assay using the synthetic growth medium described in Example 1, supplemented with 1 mM $CaCl_2$ and 50 mM KCl.

Figure 2A:
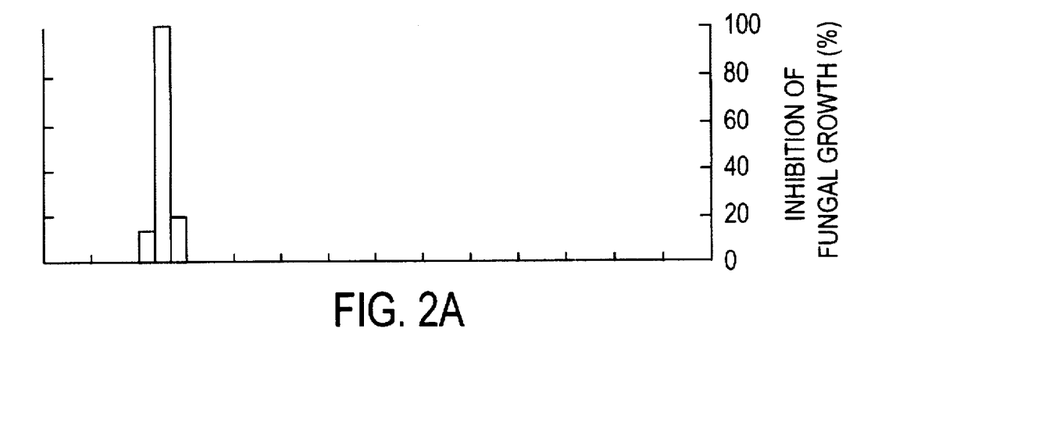
FIG. 2 shows the reversed phase chromatogram for purified Hs-AFP1.
Figure 2B:
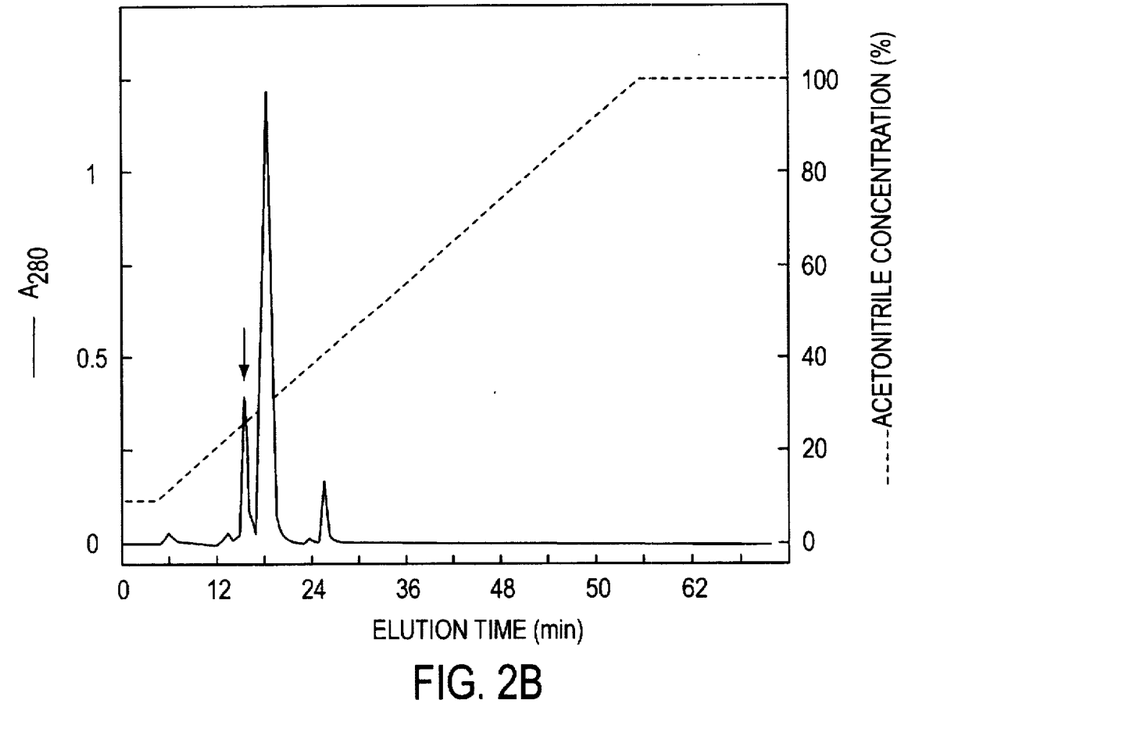

FIG. 2 shows the reversed phase chromotogram of the active fraction purified by cation exchange chromatography. The lower panel shows monitoring of the eluate for protein by measurement of the absorbance at 280 mm. The upper panel shows the antifungal activity as tested by the microspectrophotometric assay. The chromatogram shows three peaks of which the first, eluting at 25% acetonitrile contains all antifungal activity. The active factor isolated from this peak (indicated by an arrowhead on FIG. 2) is called Hs-AFP1 (*Heuchera sancuinea*—Antifungal Protein 1).

Figure 3A:
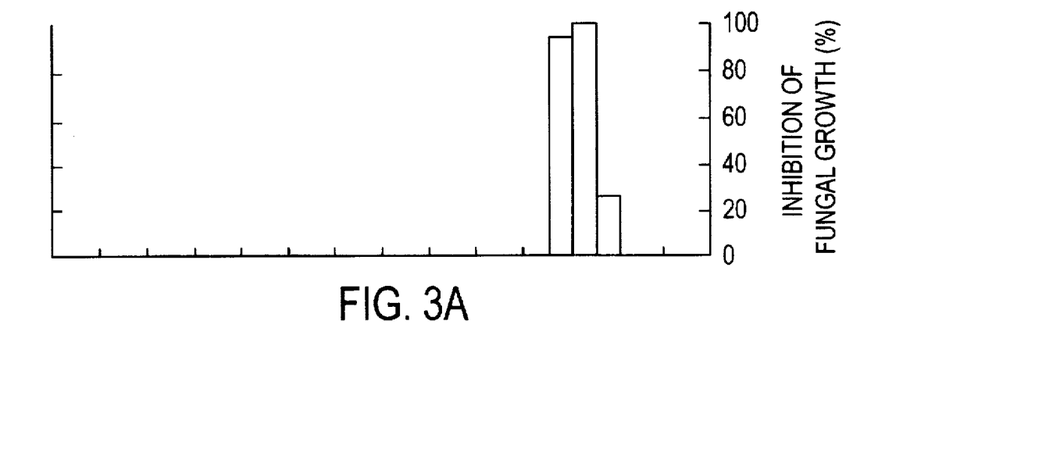
FIG. 3 shows the cation exchange chromatogram for purification of Ah-AMP1 and the associated graph of fungal growth inhibition.
Figure 3B:
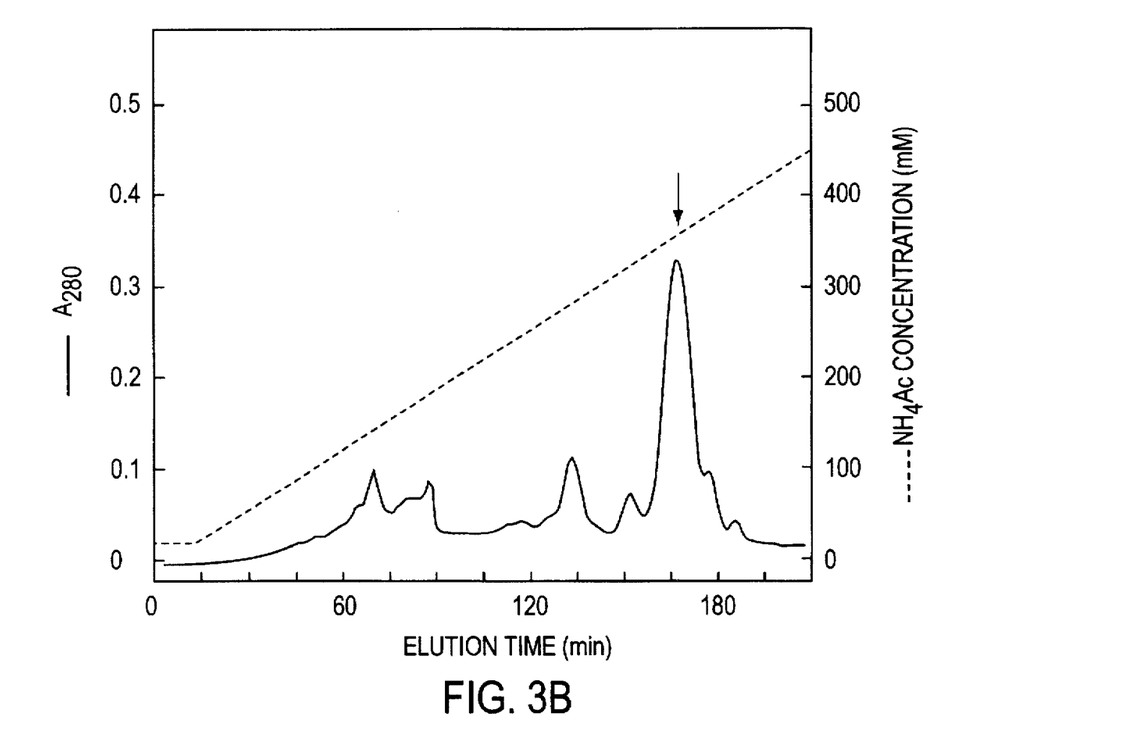
Figure 4A:
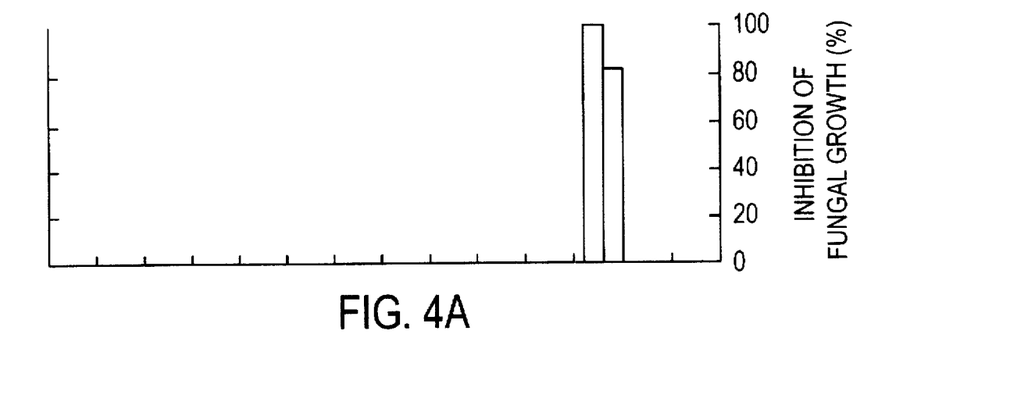
FIG. 4 shows the reversed phase chromatogram for purified Ah-AMP1.
Figure 4B:
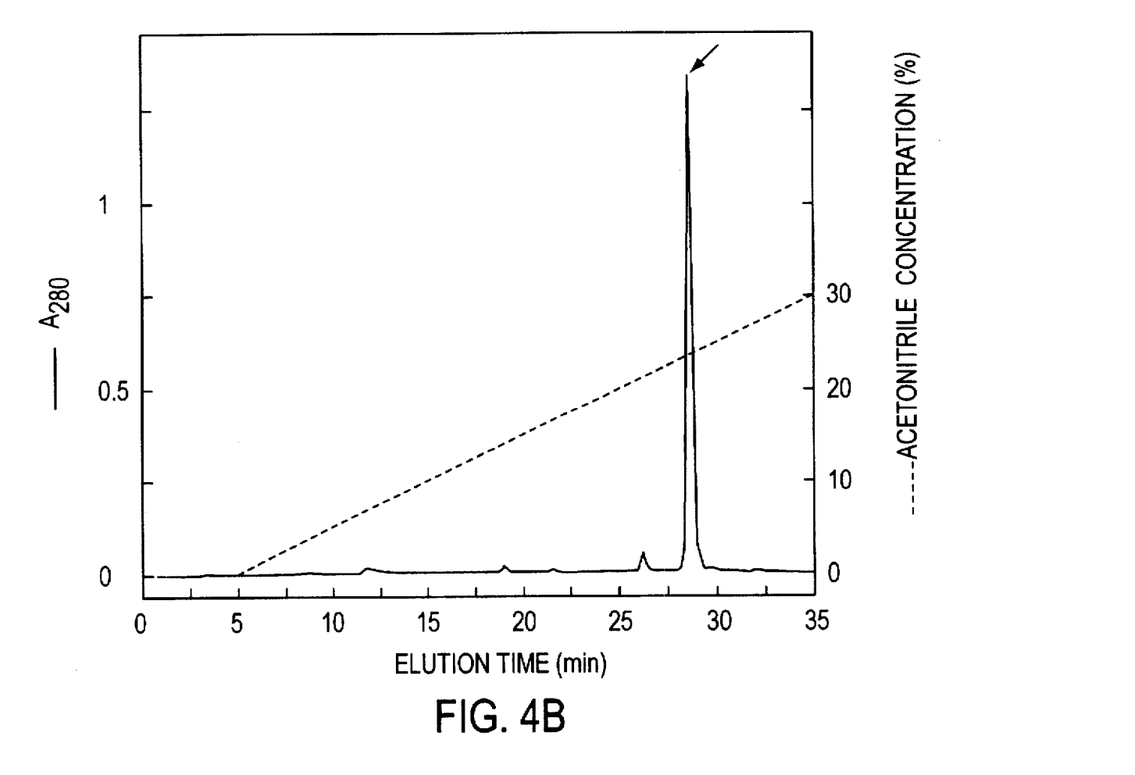

EXAMPLE 3
Purification of antifungal protein from *Aesculus hippocastanum* seeds Seeds of *Aesculus hippocastanum* (Horse Chestnut) were collected from horse chestnut trees. The seeds were pealed and 100 g of pealed seeds was lyophilyzed. Lyophilyzed seeds were ground in a coffee mill and the resulting meal was extracted in 100 ml of ice-cold extraction buffer (see Example 1). The homogenate was squeezed through cheesecloth and clarified by centrifugation (30 min at 7,000× g). The supernatant was dialyzed extensively against distilled water using benzoylated cellulose tubing (Sigma, St Louis, Mo.). After dialysis the solution was adjusted to 50 mM $NH_4Ac$ (pH 9) by addition of the ten-fold concentrated buffer and passed over a Q-Sepharose Fast Flow (Pharmacia, Uppsala, Sweden) column (12×5 cm) equilibrated in 50 mM $NH_4Ac$ (pH 9). The protein fraction which passed through the column was lyophilyzed and finally redissolved in 50 ml 20 mM $NH_4Ac$ (pH6). This fraction was applied to a S-Sepharose High Performance (Pharmacia) column (10× 1.6 cm) equilibrated in 50 mM $NH_4Ac$, pH 6.0. The column was eluted at 1 ml\min with a linear gradient of 20–500 ml $NH_4Ac$, pH 6.0 over 210 minutes. The eluate was monitored for protein by online measurement of the absorbance at 280 nm (results shown in the lower panel of FIG. 3) and collected in 7.5 ml fractions. Samples from each fraction were lyophilyzed, redissolved in 7.5 ml distilled water. Of these samples 5 μl was tested in the microspectrophotometric antifungal activity assay using the synthetic growth medium supplemented with 1 mM $CaCl_2$ and 50 mM KCl (results shown in the upper panel of FIG. 3). Following chromatography, the antifungal activity coeluted with the major peak, which eluted at around 300 mM $NH_4Ac$ (indicated by an arrowhead in FIG. 3). The fraction showing highest antifungal activity was further purified by reversed-phase chromatography. This fraction was loaded on a PEP-S (porous silica $C_2/C_{18}$, Pharmacia) column (25×0.4 cm) equilibrated with 0.1% TFA (trifluoroacetic acid). The column was developed at 1 ml/min with a linear gradient of 0.1% TFA to 50% acetonitrile/0.1% TFA over 50 minutes. The eluate was monitored for protein by online measurement of the absorption at 280 nm (results shown in the lower panel of FIG. 4), one ml fractions were collected, vacuum-dried, and dissolved in 0.5 ml distilled water. 5 μl from each fraction was assayed for antifungal activity (results shown in the upper panel of FIG. 4). The material yielded a single peak of activity, eluting at 25% acetonitrile. This represents the purified protein Ah-AMP1 (*Aesculus hippocastanum*—Antifungal Protein 1).

EXAMPLE 4
Molecular structure of the purified antifungal proteins, Hs-AFP1 and Ah-AMP1

The molecular structure of the purified antifungal proteins was further analysed by sodium dodecyl sulphate polyacrylamide gel electrophoresis (SDS-PAGE). SDS-PAGE was performed on precast commercial gels (PhastGel High Density from Pharmacia) using a PhastSystem (Pharmacia) electrophoresis apparatus. The sample buffer contained 200 mM Tris-HCl (pH 8.3), 1% (w/v) SDS, 1 mM EDTA, 0.005% bromophenol blue and, unless otherwise stated, 1% (w/v) dithioerythritol (DTE). Two hundred nanograms of the proteins were separated on the gels. Myoglobin fragments were used as molecular weight markers (Pharmacia) with the following sizes: 17 kDa, 14.5 kDa, 8 kDa, 6 kDa, and 2.5 kDa. Proteins were fixed after electrophoresis in 12.5% glutaraldehyde and silver-stained according to Heukeshoven and Dernick (1985, Electrophoresis, 6, 103–112).

After reduction of the cysteine residues by DTE, Hs-AFP1 shows a single band with an apparent molecular mass of about 5 kDa. Unreduced Hs-AFP1 migrates as a single band of about 10 kDa. These results show that the native Hs-AFP1 may be an oligomeric protein, most probably consisting of a dimer of the 5 kDa polypeptide. The oligomeric structure appears to be stabilised by disulphide linkages.

EXAMPLE 5
Antifungal and antibacterial potency

The antifungal potency of the purified proteins was assessed on different plant pathogenic fungi, using the assay described in Example 1. Growth of fungi, collection and harvest of fungal spores and preparation of mycelial fragments were done as previously described (Broekaert et al.

in Example 1; ND=not determined; Sp=spores; PrSp=spores pregerminated in the medium for 24 hours; MF=mycelial fragments preincubated for 48 hours in the medium prior to addition of the proteins; BHR=broad host range; SF=saprophytic fungus; SMF-=synthetic growth medium as described in Example 1; SMF+=SMF- supplemented with 1 mM $CaCl_2$ and 50 mM KCl; ½PDB-=half strength potato dextrose broth as described in Example 1; ½PDB+=½PDB- supplemented with 1 mM $CaCl_2$ and 50 mM KCl.

TABLE 1

ANTIFUNGAL ACTIVITY OF THE HS-AFP1 AND AH-AMP2 PROTEINS

| FUNGUS | STRAIN NUMBER | HOST SPECIES | MEDIUM | INOCULUM | PERIOD OF INCUBATION IN AFP-SOLUTION | $IC_{50}$ (µg/ml) Ah-AMP1 | Hs-AFP1 |
|---|---|---|---|---|---|---|---|
| Curvularia affinis | FAJ97 | Musa | SMF- | Sp | 40 | 0.75 | ND |
| Curvularia affinis | FAJ97 | Musa | SMF+ | Sp | 40 | 25 | ND |
| Gloeosporium musarum | FAJB6 | Musa | SMF- | Sp | 40 | <0.75 | ND |
| Gloeosporium musarum | FAJ86 | Musa | SMF+ | Sp | 40 | 12.5 | ND |
| Acremonium hyalinum | FAJ98 | Musa | SMF- | Sp | 64 | <0.75 | ND |
| Acremonium hyalinum | FAJ98 | Musa | SMF+ | Sp | 64 | 12.5 | ND |
| Glomerella cingulata | FAJ76 | Musa | SMF- | Sp | 64 | <0.75 | ND |
| Glomerella cingulata | FAJ76 | Musa | SMF+ | Sp | 64 | 12.5 | ND |
| Mycoshpaerella fijiensis | FUL549 | Musa | ½PDB+ | MF | 96 | 0.75 | 12.5 |
| Botrytis cinerea | K1147 | BHR | ½PDB- | Sp | 48 | 25 | 6 |
| Botrytis cinerea | K1147 | BHR | ½PDB+ | Sp | 48 | >100 | 25 |
| Alternaria longipes | CBS620.83 | Nicotiana | SMF- | Sp | 70 | 25 | 0.75 |
| Alternaria longipes | CBS620.83 | Nicotiana | SMF+ | Sp | 70 | 100 | 6 |
| Alternaria brassicae | | Brassica | SMF- | Sp | 66 | 1.5 | 1.5 |
| Alternaria brassicae | | Brassica | SMF+ | Sp | 66 | 3 | 3 |
| Alternaria brassicola | MUCL20297 | Brassica | SMF- | Sp | 48 | 1.5 | ND |
| Alternaria brassicola | MUCL20297 | Brassica | SMF+ | Sp | 48 | 12 | ND |
| Leptospaeria maculans | LM36uea | Brassica | ½PDB- | Sp | 48 | 0.5 | 25 |
| Leptospaeria maculans | LM36uea | Brassica | ½PDB+ | Sp | 48 | 6 | >100 |
| Leptospaeria maculans | SES1 | Brassica | ½PDB+ | PrSp | 120 | <0.75 | >100 |
| Leptospaeria maculans | SES2 | Brassica | ½PDB+ | PrSp | 120 | <0.75 | >100 |
| Cercospora beticola | SES | Beta | ½PDB+ | PrSp | 72 | 1.5 | 1.5 |
| Fusarium culmorum | IMI180420 | Cereals | SMF- | Sp | 48 | 1.5 | 0.5 |
| Fusarium culmorum | IMI180420 | Cereals | SMF+ | Sp | 48 | 25 | 1 |
| Fusarium culmorum | K0311 | Cereals | ½PDB- | Sp | 48 | 12 | 1 |
| Fusarium culmorum | K0311 | Cereals | ½PDB+ | Sp | 48 | >100 | 3 |
| Septoria tritici | K1097 | Triticum | ½PDB- | Sp | 48 | 0.5 | 0.5 |
| Septoria tritici | K1097 | Triticum | ½PDB+ | Sp | 48 | 1.5 | 3 |
| Ascochyta pisi | MUCL30164 | Pisum | SMF- | Sp | 48 | 0.8 | 1.5 |
| Ascochyta pisi | MUCL30164 | Pisum | SMF+ | Sp | 48 | 15 | >5 |
| Penicillum digitatum | K0679 | Citrus fruit | ½PDB- | Sp | 48 | 6 | 1 |
| Penicillum digitatum | K0879 | Citrus fruit | ½PDB+ | Sp | 48 | 25 | 3 |
| Verticillium albo-atrum | K0937 | Lycoperisicum | ½PDB- | Sp | 48 | 6 | 12 |
| Verticillium albo-atrum | K0937 | Lycoperisicum | ½PDB+ | Sp | 48 | >100 | 30 |
| Cladosporium sphaerospermum | K0791 | SF | ½PDB- | Sp | 48 | 0.5 | 1 |
| Cladosporium sphaerospermum | K0791 | SF | ½PDB+ | Sp | 48 | 12 | 3 |
| Trichoderma viride | K1127 | SF | ½PDB- | Sp | 48 | >100 | 15 |
| Trichoderma viride | K1127 | SF | ½PDB+ | Sp | 48 | >100 | >100 |

1990, FEMS Microbiol Lett, 69:55–60). Serial dilutions of the antifungal proteins were applied to the fungi, either using growth medium SMF- (the synthetic growth medium of Example 1), medium SMF+ (medium SMF- supplemented with 1 mM $CaCl_2$ and 50 mM KCl), growth medium ½ PDB- (half strength potato dextrose broth as in Example 1) or growth medium ½ PDB+ (medium ½ PDB- supplemented with 1 mM $CaCl_2$ and 50 mM Kcl). The percent growth inhibition was measured by microspectrophotometry. The concentration required for 50% growth inhibition after 48 h of incubation ($IC_{50}$ value) was calculated from the dose-reponse curves.

The results for Hs-AFP1 and Ah-AMP1 are summarised in Table 1. The abbreviations used are: $IC_{50}$=concentration required for 50% growth inhibition determined as described The results in Table 1 illustrate the wide range of antifungal activity possessed by the Ah-AMP1 and Hs-AFP1 proteins. The results in Table 1 also show that Hs-AFP1 and Ah-AMP1 have a somewhat different activity spectrum. For example, AH-AMP1 is highly active in ½PDB+ on Leptospaeria maculans but Hs-AFP1 is not, where as Hs-AFP1 is highly active in ½PDB+ on Fusarium culmorum but AH-AMP1 is not. The two proteins may thus be used to complement each other as a combined antimicrobial agent, combatting a wider range of diseases more effectively.

In media SMF+ and ½PDB+ containing salt additives to reflect the ionic strength of physiological conditions in plant tissues), the activity of both proteins is reduced compared to their activity in media SMF- or ½PDB-. The salt-dependent activity reduction is clearly dependent on the test organism.

11

For example, the reduction of activity in medium SMF− versus SMF+ for AH-AMP1 is two-fold on *Alternaria brassicae* and more than ten-fold on *Gloeosporium musarum*.

Hs-AFP1 and Ah-AMP1 both interfere with fungal growth processes, shown by a reduction in hyphal length. Hs-AFP1 also causes hyper-branching of hyphae of *Fusarium culmorum*. A similar effect is produced by the the antifungal proteins Rs-AFP1 and Rs-AFP2 from *Raphanus sativus* seeds (Terras FRG et al, 1992, J Biol Chem, 267:15301–15309). Ah-AMP1 does not cause hyper-branching of *Fusarium culmorum* hyphae; its mode of hyphal growth inhibition is very similar to that of the antifungal proteins Dm-AMP1, Cb-AMP1, Ct-AMP1 and Lc-AFP from Dahlia, Cnicus, Clitorea and Lathyrus respectively (International Patent Application Publication Number WO93/05153).

The antibacterial activities of Ah-AMP1 and Hs-AFP1 were measured on four gram positive bacteria (*Bacillus subtilis* JHCC 553331; *Micrococcus luteus* ATCC 93411; *Staphylococcus aureus* ATCC 25923; *Streptococcus feacolis* ATCC 29212) and two gram negative bacteria (*Eschericia coli* HB101 and *Proteus vulgaris* JHCC 558711). Hs-AFP1 did not inhibit the growth of these bacteria tested at rates of 200 µg/ml, whereas Ah-AMP1 inhibited growth of *B subtilis* at 100 µg/ml.

EXAMPLE 6

Inhibition of α-amylase

A crude α-amylase extract was prepared from dissected guts of adult cockroaches (*Blatta orientalis*) by homogenising in 20 mM Tris/HCl, pH 7.5, 10 mM CaCl$_2$ and removal of cell-debris by centrifugation. Human and porcine α-amylases were purchased from Sigma. Type 1-α-amylase inhibitor from wheat (purchased from Sigma) was used as a positive control. Amylase extracts were incubated with peptides for 20 min at 30° C. prior to addition of starch and enzyme activity was detected using the method of Bernfeld (1955, Methods Enzymol, Colwick and Kaplan eds, vol 1:149–158).

The α-amylase inhibition activities of Hs-AFP1 and Ah-AMP1 were compared on α-amylases from the three sources to that of the *Sorgum bicolor* homologue SIα3, previously reported to inhibit insect gut α-amylases (Bloch and Richardson, 1991, FEBS Lett, 279:101–104). SIα3 inhibited the activity of the enzymes from insect gut and human saliva to greater than 70% at rates as low as 5 µg/ml. Comparable inhibition was achieved with 10 U/ml of a commercial preparation of type 1 α-amylase inhibitor from wheat. SIα3 was essentially inactive on the enzyme from porcine pancreas as previously reported by Bloch and Richardson (1991).

In contrast, no inhibition of α-amylase activity was observed with Hs-AFP1 or Ah-AMP1 tested on the three enzymes even when included at rates as high as 200 µg/ml.

EXAMPLE 7

Amino acid sequencing of Hs-AFP1 and Ah-AMP1

Cysteine residues of the antifungal proteins were modified by S-pyridylethylation using the method of Fullmer (1984, Anal Biochem, 142, 336–341). Reagents were removed by HPLC on a Pep-S (porous silica $C_2/C_{18}$) (Pharmacia) column (25×0.4 cm). The S-pyridyl ethylated proteins were recovered by eluting the column with a linear gradient from 0.1% trifluoroacetic acid (TFA) to acetonitrile containing 0.1% TFA. The resulting protein fractions were subjected to amino acid sequence analysis in a 477A Protein Sequence (Applied Biosystems) with on-line detection of phenylthio-hydantoin amino acid derivatives in a 120A Analyser (Applied Biosystems).

The amino acid sequence of Hs-AFP1 and Ah-AMP1 were determined by N-terminal automated Edman degradation. The complete amino acid sequence for Hs-AFP1 is given as SEQ ID NO 1, and the complete amino acid sequence for Ah-AMP1 is given as SEQ ID NO 2.

Hs-AFP1 is 54 amino acids in length, and Ah-AMP1 is 50 amino acids in length. Both proteins contain eight cysteines and basic amino acid residues are relatively abundant.

Hs-AFP1 contains a tyrosine residue at position 41, a phenylalanine residue at position 43 and a proline residue at position 44. Identical amino acids are found in corresponding positions of Rs-AFP1 and Rs-AFP2 (Y at position 38, F at position 40, P at position 41), but are replaced by non-homologous amino acid residues in Ah-AMP1 and the other Rs-AFP-type proteins. A study of the 3-dimensional folding of a related protein from wheat seeds (Bruix et al, 1993, Biochemistry, 32:715–724) indicates that these conserved amino acids are located on a protein loop connecting two antiparallel β-sheets. This loop may be part of the active site that is responsible for interaction with putative receptor (s) on fungal hyphae.

It is noteworthy that Rs-AFP1, Rs-AFP2 and Hs-AFP1 all cause hyperbranching of fungi, whereas Ah-AMP1, Dm-AMP1, Dm-AMP2, Cb-AMP1 and Cb-AMP2 do not. This indicates that each group of proteins may be interacting either with a different target in the fungus or with the same target in a distinct way.

---

We claim:

1. An isolated protein which has the amino acid sequence shown in SEQ ID NO 1.

2. An isolated protein which has the amino acid sequence shown in SEQ ID NO 2.

3. A composition comprising the isolated protein as claimed in either claim 1 or claim 2.

4. The composition of claim 3 comprising the isolated protein which has the amino acid sequence shown in SEQ ID NO:1 and the isolated protein which has the amino acid sequence shown in SEQ ID NO:2.

5. A process of combating fungi or bacteria comprising exposure of the fungi or bacteria to an isolated or recombinant protein which has an amino acid sequence selected from the group consisting of SEQ ID NO:1 and SEQ ID NO:2.

* * * * *

SEQUENCE LISTING ( 1 ) GENERAL INFORMATION:

( i i i ) NUMBER OF SEQUENCES: 13

( 2 ) INFORMATION FOR SEQ ID NO: 1:

( i ) SEQUENCE CHARACTERISTICS:
( A ) LENGTH: 54 amino acids
( B ) TYPE: amino acid
( C ) STRANDEDNESS: single
( D ) TOPOLOGY: linear ( i i ) MOLECULE TYPE: protein (v i) ORIGINAL SOURCE:
  (A) ORGANISM: Hs-AFP1

(x i) SEQUENCE DESCRIPTION: SEQ ID NO: 1:

| Asp | Gly | Val | Lys | Leu | Cys | Asp | Val | Pro | Ser | Gly | Thr | Trp | Ser | Gly | His |
|---|---|---|---|---|---|---|---|---|---|---|---|---|---|---|---|
| 1 | | | | 5 | | | | | 10 | | | | | 15 | |
| Cys | Gly | Ser | Ser | Ser | Lys | Cys | Ser | Gln | Gln | Cys | Lys | Asp | Arg | Glu | His |
| | | | 20 | | | | | 25 | | | | | 30 | | |
| Phe | Ala | Tyr | Gly | Gly | Ala | Cys | His | Tyr | Gln | Phe | Pro | Ser | Val | Lys | Cys |
| | | | 35 | | | | 40 | | | | | 45 | | | |
| Phe | Cys | Lys | Arg | Gln | Cys |
| | | | | | 50 |

(2) INFORMATION FOR SEQ ID NO: 2:

(i) SEQUENCE CHARACTERISTICS:
    (A) LENGTH: 50 amino acids
    (B) TYPE: amino acid
    (C) STRANDEDNESS: single
    (D) TOPOLOGY: linear (i i) MOLECULE TYPE: protein (v i) ORIGINAL SOURCE:
    (A) ORGANISM: Ab-AMP1

(x i) SEQUENCE DESCRIPTION: SEQ ID NO: 2:

| Leu | Cys | Asn | Glu | Arg | Pro | Ser | Gln | Thr | Trp | Ser | Gly | Asn | Cys | Gly | Asn |
|---|---|---|---|---|---|---|---|---|---|---|---|---|---|---|---|
| 1 | | | | 5 | | | | | 10 | | | | | 15 | |
| Thr | Ala | His | Cys | Asp | Lys | Gln | Cys | Gln | Asp | Trp | Glu | Lys | Ala | Ser | His |
| | | | 20 | | | | | 25 | | | | | 30 | | |
| Gly | Ala | Cys | His | Lys | Arg | Glu | Asn | His | Trp | Lys | Cys | Phe | Cys | Tyr | Phe |
| | | | 35 | | | | 40 | | | | | 45 | | | |
| Asn | Cys |
| | 50 |

(2) INFORMATION FOR SEQ ID NO: 3:

(i) SEQUENCE CHARACTERISTICS:
    (A) LENGTH: 51 amino acids
    (B) TYPE: amino acid
    (C) STRANDEDNESS: single
    (D) TOPOLOGY: linear (i i) MOLECULE TYPE: protein (v i) ORIGINAL SOURCE:
    (A) ORGANISM: Rs-AFP1

(x i) SEQUENCE DESCRIPTION: SEQ ID NO: 3:

| Glx | Lys | Leu | Cys | Glu | Arg | Pro | Ser | Gly | Thr | Trp | Ser | Gly | Val | Cys | Gly |
|---|---|---|---|---|---|---|---|---|---|---|---|---|---|---|---|
| 1 | | | | 5 | | | | | 10 | | | | | 15 | |
| Asn | Asn | Asn | Ala | Cys | Lys | Asn | Gln | Cys | Ile | Asn | Leu | Glu | Lys | Ala | Arg |
| | | | 20 | | | | | 25 | | | | | 30 | | |
| His | Gly | Ser | Cys | Asn | Tyr | Val | Phe | Pro | Ala | His | Lys | Cys | Ile | Cys | Tyr |
| | | | 35 | | | | 40 | | | | | 45 | | | |
| Phe | Pro | Cys |
| | | 50 |

(2) INFORMATION FOR SEQ ID NO: 4:

(i) SEQUENCE CHARACTERISTICS:
    (A) LENGTH: 51 amino acids
    (B) TYPE: amino acid
    (C) STRANDEDNESS: single (D) TOPOLOGY: linear (ii) MOLECULE TYPE: protein (vi) ORIGINAL SOURCE:
  (A) ORGANISM: Rs-AFP2

(xi) SEQUENCE DESCRIPTION: SEQ ID NO: 4.:

| | | | | | | | | | | | | | | |
|---|---|---|---|---|---|---|---|---|---|---|---|---|---|---|
| Glx | Lys | Leu | Cys | Gln | Arg | Pro | Ser | Gly | Thr | Trp | Ser | Gly | Val | Cys | Gly |
| 1 | | | | 5 | | | | | 10 | | | | | 15 | |
| Asn | Asn | Asn | Ala | Cys | Lys | Asn | Gln | Cys | Ile | Arg | Leu | Glu | Lys | Ala | Arg |
| | | | 20 | | | | | 25 | | | | | 30 | | |
| His | Gly | Ser | Cys | Asn | Tyr | Val | Phe | Pro | Ala | His | Lys | Cys | Ile | Cys | Tyr |
| | | 35 | | | | | 40 | | | | | 45 | | | |
| Phe | Pro | Cys | | | | | | | | | | | | | |
| | 50 | | | | | | | | | | | | | | |

(2) INFORMATION FOR SEQ ID NO: 5:

(i) SEQUENCE CHARACTERISTICS:
    (A) LENGTH: 50 amino acids
    (B) TYPE: amino acid
    (C) STRANDEDNESS: single
    (D) TOPOLOGY: linear (ii) MOLECULE TYPE: protein (vi) ORIGINAL SOURCE:
    (A) ORGANISM: Dm-AMP1

(xi) SEQUENCE DESCRIPTION: SEQ ID NO: 5:

| | | | | | | | | | | | | | | | |
|---|---|---|---|---|---|---|---|---|---|---|---|---|---|---|---|
| Glu | Leu | Cys | Glu | Lys | Ala | Ser | Lys | Thr | Trp | Ser | Gly | Asn | Cys | Gly | Asn |
| 1 | | | | 5 | | | | | 10 | | | | | 15 | |
| Thr | Gly | His | Cys | Asp | Asn | Gln | Cys | Lys | Ser | Trp | Glu | Gly | Ala | Ala | His |
| | | | 20 | | | | | 25 | | | | | 30 | | |
| Gly | Ala | Cys | His | Val | Arg | Asn | Gly | Lys | His | Met | Cys | Phe | Cys | Tyr | Phe |
| | | | 35 | | | | | 40 | | | | | 45 | | |
| Asn | Cys | | | | | | | | | | | | | | |
| | 50 | | | | | | | | | | | | | | |

(2) INFORMATION FOR SEQ ID NO: 6:

(i) SEQUENCE CHARACTERISTICS:
    (A) LENGTH: 50 amino acids
    (B) TYPE: amino acid
    (C) STRANDEDNESS: single
    (D) TOPOLOGY: linear (ii) MOLECULE TYPE: protein (vi) ORIGINAL SOURCE:
    (A) ORGANISM: Cb-AMP1

(xi) SEQUENCE DESCRIPTION: SEQ ID NO: 6:

| | | | | | | | | | | | | | | | |
|---|---|---|---|---|---|---|---|---|---|---|---|---|---|---|---|
| Glu | Leu | Cys | Glu | Lys | Ala | Ser | Lys | Thr | Trp | Ser | Gly | Asn | Cys | Gly | Asn |
| 1 | | | | 5 | | | | | 10 | | | | | 15 | |
| Thr | Lys | His | Cys | Asp | Asp | Gln | Cys | Lys | Ser | Trp | Glu | Gly | Ala | Ala | His |
| | | | 20 | | | | | 25 | | | | | 30 | | |
| Gly | Ala | Cys | His | Val | Arg | Asn | Gly | Lys | His | Met | Cys | Phe | Cys | Tyr | Phe |
| | | | 35 | | | | | 40 | | | | | 45 | | |
| Asn | Cys | | | | | | | | | | | | | | |
| | 50 | | | | | | | | | | | | | | |

(2) INFORMATION FOR SEQ ID NO:7:

( i ) SEQUENCE CHARACTERISTICS:
    ( A ) LENGTH: 49 amino acids
    ( B ) TYPE: amino acid
    ( C ) STRANDEDNESS: single
    ( D ) TOPOLOGY: linear ( i i ) MOLECULE TYPE: protein ( v i ) ORIGINAL SOURCE:
    ( A ) ORGANISM: Cb-AMP1

( x i ) SEQUENCE DESCRIPTION: SEQ ID NO: 7:

```
Asn Leu Cys Glu Arg Ala Ser Leu Thr Trp Thr Gly Asn Cys Gly Asn
1               5                   10                  15
Thr Gly His Cys Asp Thr Gln Cys Arg Asn Trp Glu Ser Ala Lys His
                20                  25                  30
Gly Ala Cys His Lys Arg Gly Asn Trp Lys Cys Phe Cys Tyr Phe Asp
                35                  40                  45
Cys
```

( 2 ) INFORMATION FOR SEQ ID NO: 8:

( i ) SEQUENCE CHARACTERISTICS:
    ( A ) LENGTH: 47 amino acids
    ( B ) TYPE: amino acid
    ( C ) STRANDEDNESS: single
    ( D ) TOPOLOGY: linear ( i i ) MOLECULE TYPE: protein ( v i ) ORIGINAL SOURCE:
    ( A ) ORGANISM: Lc-AFP ( x i ) SEQUENCE DESCRIPTION: SEQ ID NO: 8:

```
Lys Thr Cys Glu Asn Leu Ser Gly Thr Phe Lys Gly Pro Cys Ile Pro
1               5                   10                  15
Asp Gly Asn Cys Asn Lys His Cys Lys Asn Asn Glu His Leu Leu Ser
                20                  25                  30
Gly Arg Cys Arg Asp Asp Phe Xaa Cys Trp Cys Thr Arg Asn Cys
                35                  40                  45
```

( 2 ) INFORMATION FOR SEQ ID NO: 9:

( i ) SEQUENCE CHARACTERISTICS:
    ( A ) LENGTH: 47 amino acids
    ( B ) TYPE: amino acid
    ( C ) STRANDEDNESS: single
    ( D ) TOPOLOGY: linear ( i i ) MOLECULE TYPE: protein ( v i ) ORIGINAL SOURCE:
    ( A ) ORGANISM: pSAS10

( x i ) SEQUENCE DESCRIPTION: SEQ ID NO: 9:

```
Lys Thr Cys Glu Asn Leu Val Asp Thr Tyr Arg Gly Pro Cys Phe Thr
1               5                   10                  15
Thr Gly Ser Cys Asp Asp His Cys Lys Asn Lys Glu His Leu Leu Ser
                20                  25                  30
Gly Arg Cys Arg Asp Asp Val Arg Cys Trp Cys Thr Arg Asn Cys
                35                  40                  45
```

( 2 ) INFORMATION FOR SEQ ID NO: 10:

( i ) SEQUENCE CHARACTERISTICS:
    ( A ) LENGTH: 45 amino acids
    ( B ) TYPE: amino acid ( C ) STRANDEDNESS: single
( D ) TOPOLOGY: linear ( i i ) MOLECULE TYPE: protein ( v i ) ORIGINAL SOURCE:
( A ) ORGANISM: pl230

( x i ) SEQUENCE DESCRIPTION: SEQ ID NO: 10:

| Asn | Thr | Cys | Glu | Asn | Leu | Ala | Gly | Ser | Tyr | Lys | Gly | Val | Cys | Phe | Gly |
|---|---|---|---|---|---|---|---|---|---|---|---|---|---|---|---|
| 1 | | | | 5 | | | | | 10 | | | | | 15 | |

| Gly | Cys | Asp | Arg | His | Cys | Arg | Thr | Gln | Glu | Gly | Ala | Ile | Ser | Gly | Arg |
|---|---|---|---|---|---|---|---|---|---|---|---|---|---|---|---|
| | | | 20 | | | | | 25 | | | | | 30 | | |

| Cys | Arg | Asp | Asp | Phe | Arg | Cys | Trp | Cys | Thr | Lys | Asn | Cys |
|---|---|---|---|---|---|---|---|---|---|---|---|---|
| | | | 35 | | | | 40 | | | | | 45 |

( 2 ) INFORMATION FOR SEQ ID NO: 11:

( i ) SEQUENCE CHARACTERISTICS:
( A ) LENGTH: 48 amino acids
( B ) TYPE: amino acid
( C ) STRANDEDNESS: single
( D ) TOPOLOGY: linear ( i i ) MOLECULE TYPE: protein ( v i ) ORIGINAL SOURCE:
( A ) ORGANISM: Sia3

( x i ) SEQUENCE DESCRIPTION: SEQ ID NO: 11:

| Arg | Val | Cys | Met | Gly | Lys | Ser | Ala | Gly | Phe | Lys | Gly | Leu | Cys | Met | Arg |
|---|---|---|---|---|---|---|---|---|---|---|---|---|---|---|---|
| 1 | | | | 5 | | | | | 10 | | | | | 15 | |

| Asp | Gln | Asn | Cys | Ala | Gln | Val | Cys | Leu | Gln | Glu | Gly | Trp | Gly | Gly | Gly |
|---|---|---|---|---|---|---|---|---|---|---|---|---|---|---|---|
| | | | 20 | | | | | 25 | | | | | 30 | | |

| Asn | Cys | Asp | Gly | Val | Met | Arg | Gln | Cys | Lys | Cys | Ile | Arg | Gln | Cys | Trp |
|---|---|---|---|---|---|---|---|---|---|---|---|---|---|---|---|
| | | | 35 | | | | | 40 | | | | | 45 | | |

( 2 ) INFORMATION FOR SEQ ID NO: 12:

( i ) SEQUENCE CHARACTERISTICS:
( A ) LENGTH: 47 amino acids
( B ) TYPE: amino acid
( C ) STRANDEDNESS: single
( D ) TOPOLOGY: linear ( i i j MOLECULE  TYPE: protein ( v i ) ORIGINAL SOURCE:
( A ) ORGANISM: ylP ( x i ) SEQUENCE DESCRIPTION: SEQ ID NO: 12:

| Lys | Ile | Cys | Arg | Arg | Arg | Ser | Ala | Gly | Phe | Lys | Gly | Pro | Cys | Met | Ser |
|---|---|---|---|---|---|---|---|---|---|---|---|---|---|---|---|
| 1 | | | | 5 | | | | | 10 | | | | | 15 | |

| Asn | Lys | Asn | Cys | Ala | Gln | Val | Cys | Gln | Gln | Glu | Gly | Trp | Gly | Gly | Gly |
|---|---|---|---|---|---|---|---|---|---|---|---|---|---|---|---|
| | | | 20 | | | | | 25 | | | | | 30 | | |

| Asn | Cys | Asp | Gly | Pro | Phe | Arg | Arg | Cys | Lys | Cys | Ile | Arg | Gln | Cys |
|---|---|---|---|---|---|---|---|---|---|---|---|---|---|---|
| | | | 35 | | | | | 40 | | | | | 45 | | |

( 2 ) INFORMATION FOR SEQ ID NO: 13:

( i ) SEQUENCE CHARACTERISTICS:
( A ) LENGTH: 47 amino acids
( B ) TYPE: amino acid
( C ) STRANDEDNESS: single
( D ) TOPOLOGY: linear ( i i ) MOLECULE TYPE: protein (vi) ORIGINAL SOURCE:
    (A) ORGANISM: p322

(xi) SEQUENCE DESCRIPTION: SEQ ID NO: 13:

| Arg | His | Cys | Glu | Ser | Leu | Ser | His | Arg | Phe | Lys | Gly | Pro | Cys | Thr | Arg |
|---|---|---|---|---|---|---|---|---|---|---|---|---|---|---|---|
| 1 | | | | 5 | | | | | 10 | | | | | 15 | |

| Asp | Ser | Asn | Cys | Ala | Ser | Val | Cys | Glu | Thr | Glu | Arg | Phe | Ser | Gly | Gly |
|---|---|---|---|---|---|---|---|---|---|---|---|---|---|---|---|
| | | | 20 | | | | | 25 | | | | | 30 | | |

| Asn | Cys | His | Gly | Phe | Arg | Arg | Arg | Cys | Phe | Cys | Thr | Lys | Pro | Cys |
|---|---|---|---|---|---|---|---|---|---|---|---|---|---|---|
| | | 35 | | | | | 40 | | | | | 45 | | |